United States Patent
Gayar

(10) Patent No.: US 9,233,259 B2
(45) Date of Patent: Jan. 12, 2016

(54) SKIN HDR BRACHYTHERAPY MULTICHANNEL APPLICATORS AND METHODS OF BRACHYTHERAPY TREATMENT

(71) Applicant: Hesham E. Gayar, Grand Blanc, MI (US)

(72) Inventor: Hesham E. Gayar, Grand Blanc, MI (US)

( * ) Notice: Subject to any disclaimer, the term of this patent is extended or adjusted under 35 U.S.C. 154(b) by 239 days.

(21) Appl. No.: 13/796,532

(22) Filed: Mar. 12, 2013

(65) Prior Publication Data
US 2014/0275695 A1 Sep. 18, 2014

(51) Int. Cl.
*A61N 5/10* (2006.01)

(52) U.S. Cl.
CPC ....... *A61N 5/1028* (2013.01); *A61N 2005/1008* (2013.01); *A61N 2005/1095* (2013.01)

(58) Field of Classification Search
CPC ............................. A61N 5/1001; A61N 5/1028
See application file for complete search history.

(56) References Cited

U.S. PATENT DOCUMENTS

| 5,857,956 A * | 1/1999 | Liprie | 600/7 |
| 2011/0201866 A1 * | 8/2011 | Cipriani et al. | 600/1 |

OTHER PUBLICATIONS

Kron et al., "A flattening filter for brachytherapy skin irradiation," Phys. Med. Biol. 47 (2002), p. 713-722.*
Perez-Catalayud et al., "A Dosimetric Study of Leipzig Applicators," Int. J. Radiation Oncology Biol. Phys., vol. 62, No. 2, p. 579-584, 2005.*
Vynckier, "Brachytherapy", retrieved from http://www.imre.ucl.ac.be/rpr/sv2012/RDTH3120-partie3.pdf on Feb. 27, 2015, updated as of Jan. 30, 2012 (as seen on http://www.imre.ucl.ac.be/rpr/ [click on Courses Notes]).*
http://www.imre.ucl.ac.be/rpr/ (clicked on "Courses Notes", retrieved on Feb. 27, 2015).*

* cited by examiner

*Primary Examiner* — Charles A Marmor, II
*Assistant Examiner* — Thaddeus Cox
(74) *Attorney, Agent, or Firm* — Brinks Gilson & Lione

(57) ABSTRACT

Applicators for HDR brachytherapy for topical skin treatment which employ multiple channels for radioisotope sources, oriented by the applicator generally parallel to each other and to a desired treatment area skin surface. These applicators provide good radiation exposure uniformity. Filtration of undesirable low energy radiation may be employed using an attached filter element. The applicators are particularly adapted for the treatment of squamous and basal cell skin cancers or other skin lesions. The applicators may provide two or more source guides in various sizes and shapes are described.

26 Claims, 4 Drawing Sheets

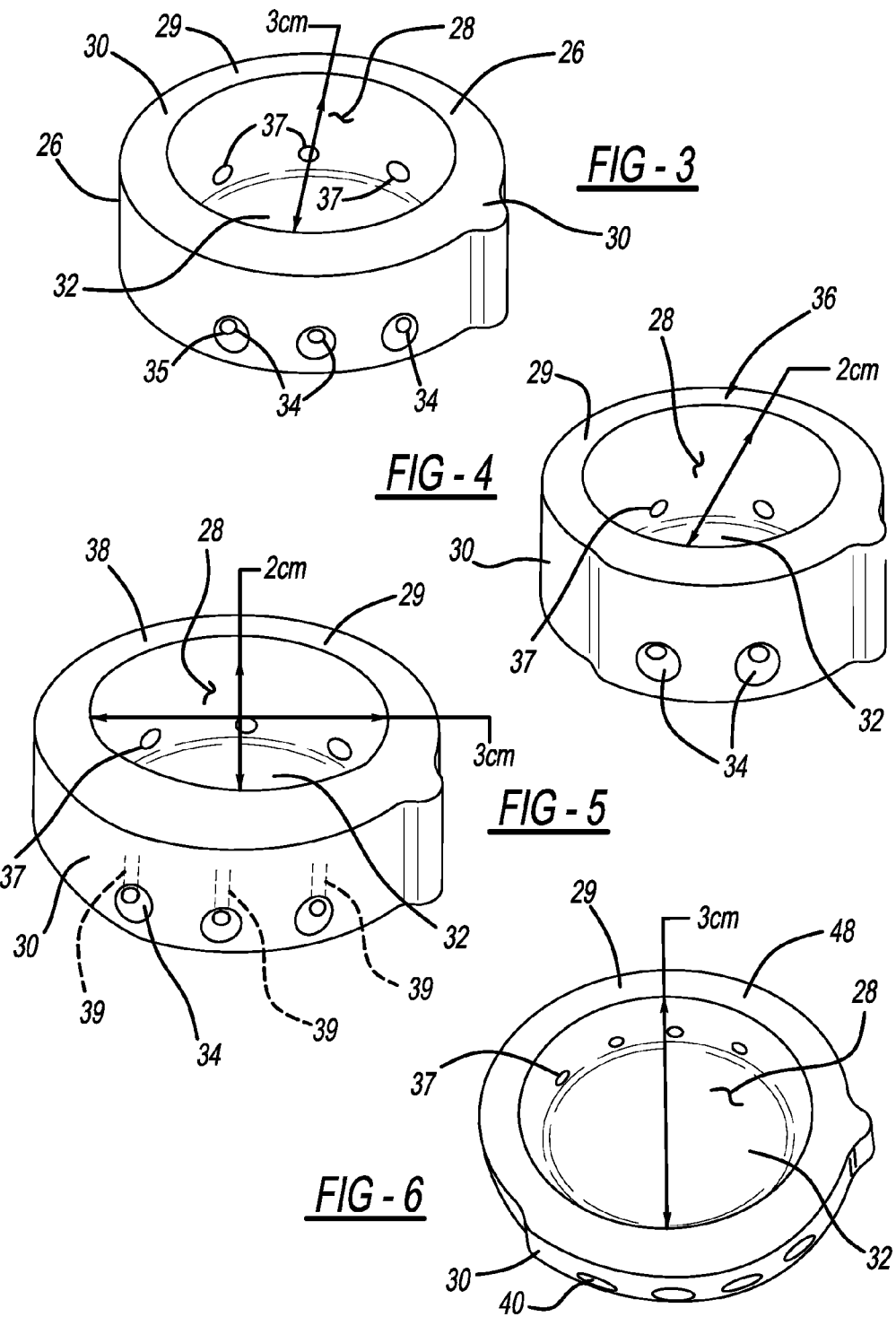

Dose Distribution

SKIN HDR BRACHYTHERAPY MULTICHANNEL APPLICATORS AND METHODS OF BRACHYTHERAPY TREATMENT

FIELD OF THE INVENTION

This invention relates to high dose rate (HDR) brachytherapy devices and methods particularly adapted for treating human skin cancers and other conditions, and specifically to applicator components used in such systems and methods for their use in patient treatment.

BACKGROUND OF THE INVENTION

Radiation treatment is very effective for the treatment of squamous cell and basal cell skin cancers for human patients. Historically, superficial 250 KV external beam radiation provided a good tool for such treatment with excellent control and cosmetic results. However, such equipment is no longer available, and is bulky, expensive, and requires highly skilled operators.

Currently, superficial radiation treatment with electron beams is provided for treating certain skin cancers through a long course of multiple therapy sessions (fractional therapy) which may require daily therapy for several weeks and the depth of the radiation dose for such therapy is usually several centimeters. Such a fractional course is long, expensive, and inconvenient to patients. In addition, cosmetic results from electron beam radiation therapy to the skin are often compromised due to irradiation of subcutaneous tissue underlying the desired treatment site which does not need to be targeted therapeutically.

In brachytherapy procedures, catheters or guide tubes are used which are, in some procedures a guide tube is used which is positioned externally at a desired orientation relative to a patient's skin area to be treated. A radioisotope source is loaded into the guide tube and is moved robotically inside the guide tube to topically expose tissue surrounding the source to a desired radiation dose and is thereafter withdrawn. This is referred to as high dose rate or HDR brachytherapy. This procedure is distinguished from low dose rate or LDR brachytherapy in which a radioisotope source is implanted for exposure over a long period (months or years) or implanted permanently. The radiation exposure dose of brachytherapy is intended to cause radiotoxicity and destroy targeted human tissue, for example cancerous skin cells.

In HDR brachytherapy for treating skin cancer, an applicator component is used which forms a fixture for supporting and orienting a brachytherapy guide tube and further for shielding radiation exposure along ray paths not providing desired exposure of the skin area to be treated. A brachytherapy treatment machine is used to accurately position the radioisotopes source in the guide tube during a treatment session. Typically the position of the radioisotope source is moved within the guide tube after stopping at dwell positions. A control wire inside a flexible brachytherapy guide tube is attached to the guide tube which is in turn mounted to the applicator. The brachytherapy treatment machine moves the radioisotope source to desired dwell positions on a time schedule within the applicator by moving the control wire.

Single channel brachytherapy applicators for treating skin cancers are known. These devices employed a single guide tube for the radioisotope source. The use of single channel brachytherapy applicators results in uneven radiation distribution to skin surface and superficial depth, resulting in a very high dose in the center area of the applicator as compared to peripheral regions in the treatment field area. Due to limitations of such devices, treatment of skin cancer has been limited due to lack of good applicators with standardized radiation distribution limited to several millimeters in depth. Another known system utilizes a single channel source oriented in a vertical orientation, which is also not conducive to uniform dose distribution pattern; this results in a very uneven dose distribution, relative low dose at center of applicator surrounded by a high dose zone then a very low dose at periphery of treatment area.

SUMMARY OF THE INVENTION

This invention is related to applicators for HDR brachytherapy for topical skin treatment which employ multiple channels for radioisotope sources, which are oriented generally parallel to each other and to the desired treatment area skin surface. These applicators provide good radiation exposure uniformity. Filtration of undesirable low energy radiation may be employed using an attached filter element. The applicators are particularly adapted for the treatment of squamous and basal cell skin cancers or other skin lesions. The applicators are used with HDR brachytherapy treatment machines that are already commercially available.

Additional benefits and advantages of the present invention will become apparent to those skilled in the art to which the present invention relates from the subsequent description of the preferred embodiment and the appended claims, taken in conjunction with the accompanying drawings.

BRIEF DESCRIPTION OF THE DRAWINGS

FIG. 3 is another pictorial view of the applicator in accordance with a first embodiment of the invention;

FIG. 4 is a pictorial view of an applicator in accordance with a second embodiment of the invention;

FIG. 5 is a pictorial view of an applicator in accordance with a third embodiment of the invention; and FIG. 6 is a pictorial view of an applicator in accordance with a fourth embodiment of the invention.

DETAILED DESCRIPTION OF THE INVENTION

Figure 1:
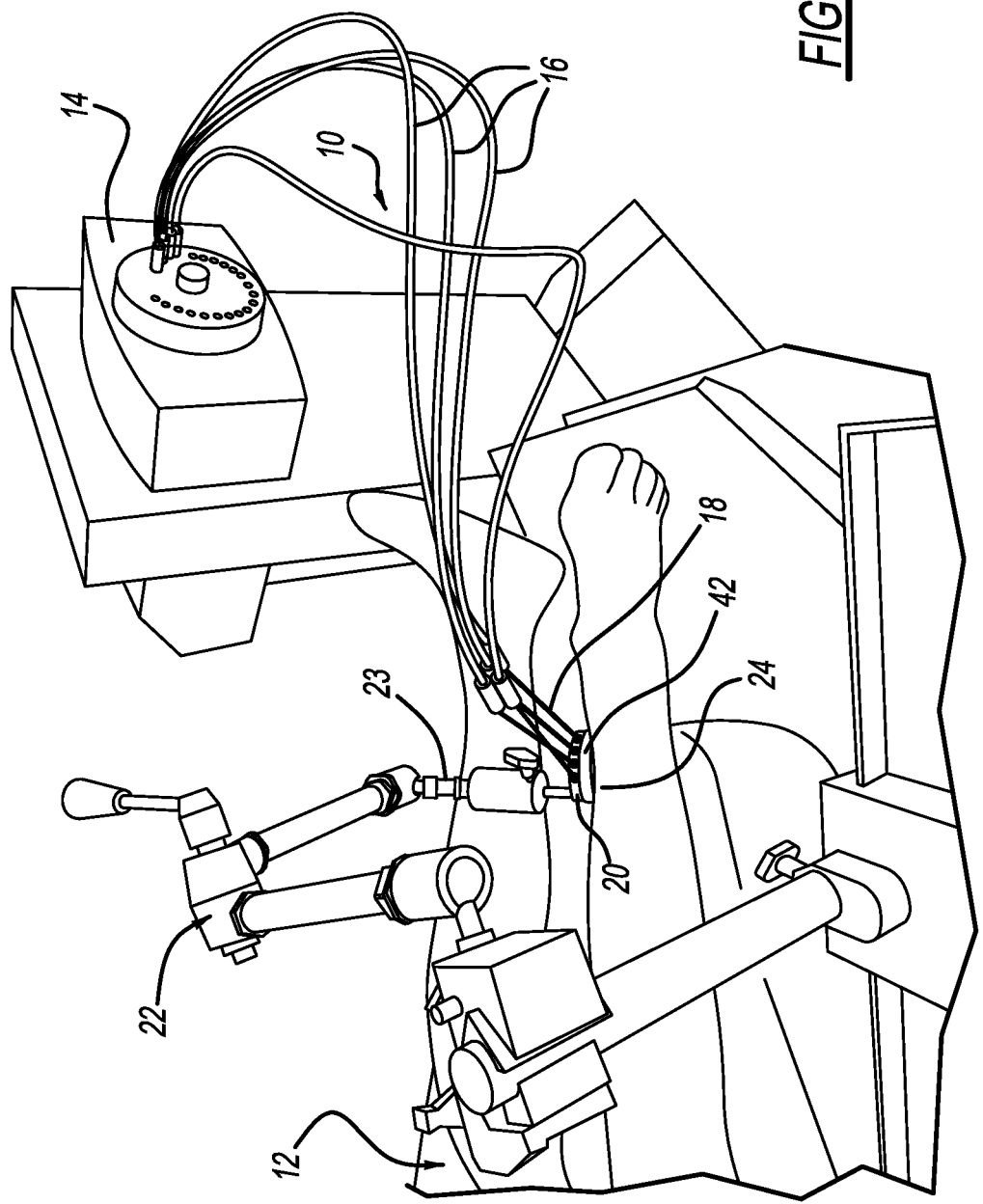
FIG. 1 is a pictorial view of an HDR treatment system incorporating one embodiment of an applicator in accordance with the present invention shown during a patient treatment session.

With reference to FIG. 1, an HDR treatment system for topical skin treatment is shown and is generally designated by reference number 10. Treatment system 10 is shown in a treatment session for a human patient 12, and principally includes HDR treatment machine 14 with a plurality of flexible tubes 16 coupled to the machine and terminate at guide tubes 18 affixed to applicator 20. Applicator 20 as illustrated is in accordance with one embodiment of the present invention.

Applicator 20 is positioned adjacent a desired skin treatment area using jointed holding fixture 22 which can be adjusted to move through many degrees of freedom to properly position applicator 20 as desired for treatment. Fixture 22 has elbow joints which when locked holds the fixture arm 23 in a steady position. Also, at the tip of the arm 23 where the applicator is affixed, there is a micro adjustment system which allows the applicator face to be positioned close to the treatment area skin surface.

In accordance with known brachytherapy treatment systems, machine 14 is used for and after loading treatment process and is programmed to advance one or more a radioisotope radiation sources (not shown), first through flexible transfer tubes 16 and then into guide tubes 18. Commercially available HDR Brachytherapy treatments machines like Gamma Med Plus (Varian) and Nucletron High Dose Rate machines are examples of those which may be used with the present invention. As will be described in greater detail in the following text, machine 14 is programmed in accordance with a prescribed treatment plan to accurately move the radiation sources along a prescribed schedule of dwell positions within the guide tubes 18 as desired to provide a desired distribution of radiation exposure over the patient treatment area 24. In a treatment session, patient 12 is immobilized to the extent necessary to hold treatment area 24 in a fixed position relative to applicator 20 during a treatment session.

Figure 2:
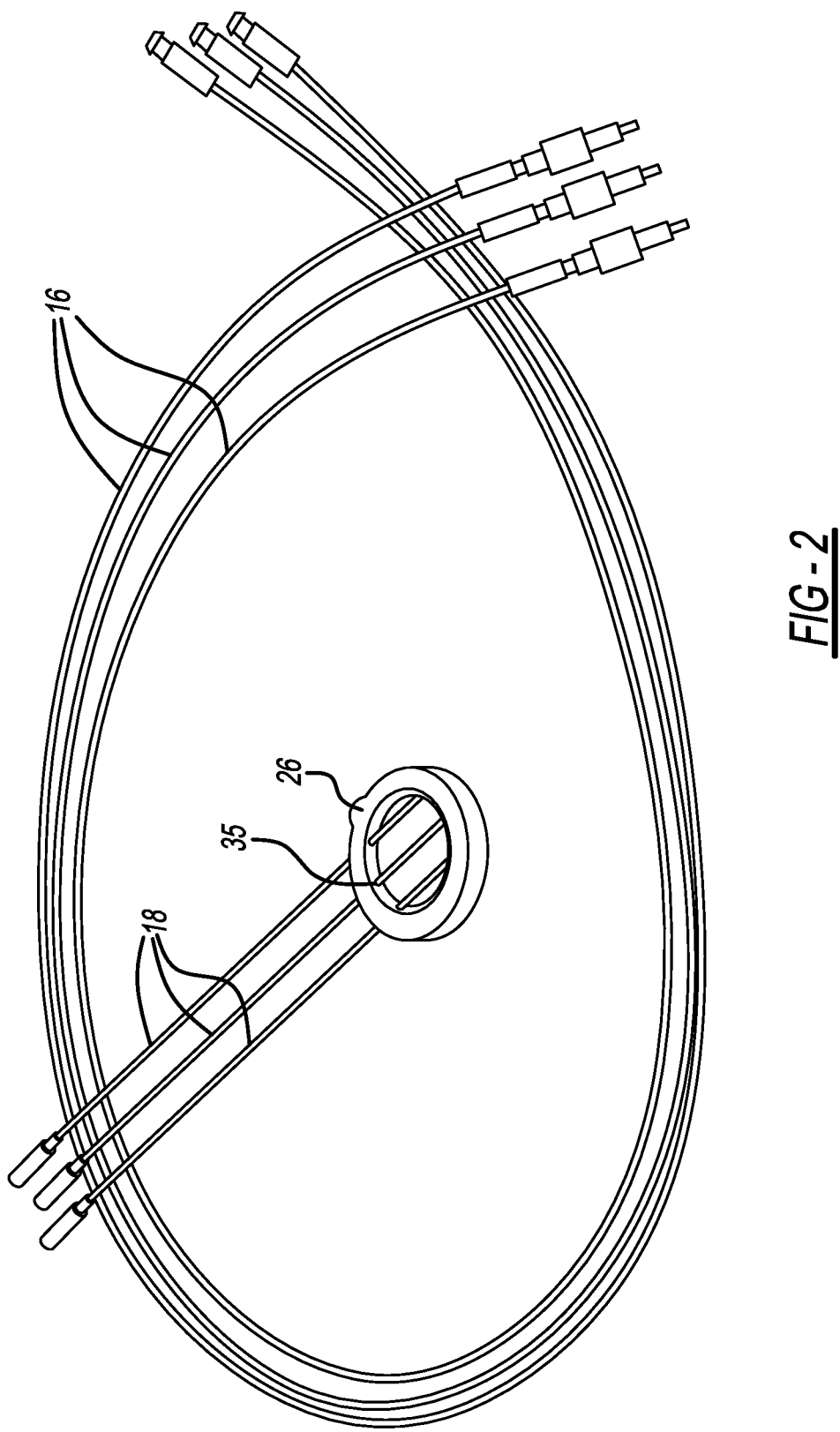
FIG. 2 is a pictorial view of an applicator in accordance with a first embodiment of this invention shown with installed guide tubes and related components.

Several embodiments of applicators 20 are described in accordance with the present invention. FIGS. 2 and 3 illustrate 3 cm diameter applicator 26 in accordance with an embodiment of this invention. As shown applicator 26 forms a concave cavity 28 with a perimeter annular upstanding wall 30 with an enclosed bottom surface 32. The upper edge of wall 30 forms a flat annular face surface 29. Not shown is the bottom surface of applicator 26 which is flat. Applicator 26 is preferably formed from a metallic material capable of providing radiation shielding such as tungsten. Three bores 34 are formed through the upstanding wall 30 provided for positioning three rigid guide tubes 18 in position as illustrated in FIG. 2. Each bore 34 includes open bore section 35 through wall 30 which are aligned with blind bore sections 37 which do not penetrate through wall 30. Bores 34 are mutually parallel. Various means for affixing rigid guide tubes 18 in their position in a respective bore 34 can be used such as mechanical set screw type fixing systems. Threaded bores 39 are shown which extend from the outside bottom surface of the applicator and intersect bores 34 which allow a set screw to be installed. Once fixed in position within bores 34, rigid guide tubes 18 are positioned such that there longitudinal axes are generally parallel to face surface 29 and, during treatment, are parallel to the skin surface at patient treatment area 24.

FIG. 2 illustrates applicator 26 with rigid guide tubes 18 affixed in position within bores 34 and shown with detached transfer tubes 16. Guide tubes 18 may be provided formed of various in different materials, for example stainless steel, titanium, or plastic Now with reference to FIG. 4, a second embodiment of an applicator 36 in accordance with the present invention is illustrated. Elements and features of applicator 36 which are identical to those of the first embodiment (applicator 26) are identified by like reference numbers. Applicator 36 differs from the first embodiment in that it has a smaller diameter; in this case 2 cm, and rather than having bores 34 for three guide channels, it features two guide channels.

FIG. 5 illustrates applicator 38 which differs from the prior embodiments in that it has an elliptical configuration with its major axes measuring 2×3 cm. This embodiment features three guide channels.

FIG. 6 illustrates applicator 40 which is generally identical to applicator 38 except that it has a larger diameter of 4 cm. Applicator 40 provides four bores 34 for four guide tubes 18.

The following Table 1 provides dimensional features and material for the applicators 26, 36, 38, and 40, identified by their major dimensions as presented previously (i.e. 2 cm is applicator 26, etc.). In the table, the Outer Height indicates the height of wall 30, the Inner Height is the height of wall 30 measured on the inside of the concave cavity 28 above bottom surface 32, and Min. Wall Thickness is the radial thickness of wall 30.

TABLE 1

| Applicator Dia | Applicator Material | Outer Height (cm) | Inner Height (cm) | Min. Wall Thickness |
|---|---|---|---|---|
| 2 cm(36) | Tungsten | 1.4 | 1.1 | 7 mm |
| 3 cm(26) | Tungsten | 1.4 | 1.1 | 7 mm |
| 4 cm(40) | Tungsten | 1.4 | 1.1 | 7 mm |
| 2 cm × 3 cm(38) | Tungsten | 1.4 | 1.1 | 7 mm |

Table 2 as follows provides additional dimensional specifications for exemplary embodiments of the present invention. In the third column, the maximum distance between the inside surface of the inside of wall 30 and the outermost guide tube 18 is indicated. The last column indicates that a preferred separation distance between the guide tubes 18 and the patient treatment area 24 is 1 cm. Since in most treatment applicator face surface 29 will be placed on or near contact with the patient's skin, this dimension is also the separation of the planes defined by face surface 29 and guide tubes 18 once installed within the applicator.

TABLE 2

| Applicator Dia | No. of Source Path Tubes (18) | Distance between source path tubes (18) | Distance between inner wall & outer source path tubes | Distance of source guide tube center to skin surface |
|---|---|---|---|---|
| 2 cm(36) | 2 | 1 cm | 0.5 cm | 1 cm |
| 3 cm(26) | 3 | 1 cm | 0.5 cm | 1 cm |
| 4 cm(40) | 4 | 1 cm | 0.5 cm | 1 cm |
| 2 cm × 3 cm(38) | 3 | 1 cm | 0.5 cm | 1 cm |

The unique design feature of these applicators 26, 36, 38, and 40 is that they provide multiple source dwell positions within the applicator cavity which are used to shape the dose distribution patterns as compared to market available applicators which use a single source with a dwell position at the center of the applicator cavity. This design helps us to better control the dose distribution within the area of irradiation. When implying the applicators in accordance with the present invention, the source dwell positions and dwell times are determined in accordance with a radiation treatment plan intended to achieve the desired results.

When connected to the HDR treatment machine 14, the radioisotope source stops in multiple dwell positions in each of the source guide tubes 18 within the associated applicator concave cavity 28. The multiple dwell positions within each applicator cavity 28 allow for better control of radiation dose distribution at the surface and depth of skin when compared to single source-dwell position applicators.

In order to filter the low energy spectrum of radiation emanating from the radioisotope sources, filter caps of plastics of for example a thickness 0.34 mm may be used. Filter 42 is shown a fixed to applicator 20 in FIG. 1. Filter 42 can be formed in a manner that allows the filter to be snap-fit over the opening of the applicator. In one exemplary embodiment of the present invention, the filter material was formed of Derlin monopolymer with a density of 0.051 (ib/in3).

The following Table 3 illustrate examples of a treatment schedule using the applicators 26, 36, 38, and 40 designated by their dimensional characteristic. Table 3 presents dwell positions for radioactive source for the bores 34 identified as Channels 1 and 2 for 2 cm. applicator 36; as channels 1, 2, and 3 for applicators 26, and 38; whereas applicator 40 has four Channels 1-4. The position numbers identified as positions #1-3, #1-4 and #1-8 designate dwell positions of the radio-isotope source along the path of the channel with the indicated separation between dwell positions (step sizes). Table 3 also provides data for various desired radiation exposure magnitudes identified as 5, 6, and 7Gy (grey). The schedules described in Table 3 are examples of treatment plans which may be prescribed to treat a particular patient treatment area 24.

TABLE 3

3.1

2 cm Circle Skin Applicator
80 IDL Rounded Aug. 25, 2010

| 5 Gy | 6 Gy | 7 Gy | Position | |
|---|---|---|---|---|
| 12.8 | 15.3 | 17.8 | 1 | CHANNEL 1 |
| 6.5 | 7.8 | 9.1 | 2 | (6 mm Step Size) |
| 12.8 | 15.3 | 17.8 | 3 | |
| 12.8 | 15.3 | 17.8 | 1 | CHANNEL 2 |
| 6.5 | 7.8 | 9.1 | 2 | (6 mm Step Size) |
| 12.8 | 15.3 | 17.8 | 3 | |
| 64.2 | 76.8 | 89.4 | seconds | |

3.2

3 cm Circle Skin Applicator
80 IDL Rounded Aug. 25, 2010

| 5 Gy | 6 Gy | 7 Gy | Position | |
|---|---|---|---|---|
| 10 | 12 | 14 | 1 | CHANNEL 1 |
| 4.6 | 5.6 | 6.5 | 2 | (5 mm Step Size) |
| 4.6 | 5.6 | 6.5 | 3 | |
| 10 | 12 | 14 | 4 | |
| 12.1 | 14.5 | 16.9 | 1 | CHANNEL 2 |
| 3.1 | 3.8 | 4.4 | 2 | (5 mm Step Size) |
| 1.6 | 1.9 | 2.3 | 3 | |
| 1.6 | 1.9 | 2.3 | 4 | |
| 3.1 | 3.8 | 4.4 | 5 | |
| 12.1 | 14.5 | 16.9 | 6 | |
| 10 | 12 | 14 | 1 | CHANNEL 3 |
| 4.6 | 5.6 | 6.5 | 2 | (5 mm Step Size) |
| 4.6 | 5.6 | 6.5 | 3 | |
| 10 | 12 | 14 | 4 | |
| 92 | 110.8 | 129.2 | seconds | |

3.3

4 cm Circle Skin Applicator
80 IDL Rounded Mar. 7, 2012

| 5 Gy | 6 Gy | 7 Gy | Position | |
|---|---|---|---|---|
| 11.7 | 14 | 16.3 | 1 | CHANNEL 1 |
| 6.7 | 8 | 9.3 | 2 | (5 mm Step Size) |
| 5.0 | 6 | 7 | 3 | Origin 1 mm |
| 6.7 | 8 | 9.3 | 4 | |
| 11.7 | 14 | 16.3 | 5 | |
| 11.7 | 14 | 16.3 | 1 | CHANNEL 2 |
| 5.8 | 7 | 8.2 | 2 | (5 mm Step Size) |
| 2.9 | 3.5 | 4.1 | 3 | Origin 0 mm |
| 2.1 | 2.5 | 2.9 | 4 | |

TABLE 3-continued

| 2.1 | 2.5 | 2.9 | 5 | |
|---|---|---|---|---|
| 2.9 | 3.5 | 4.1 | 6 | |
| 5.8 | 7 | 8.2 | 7 | |
| 11.7 | 14 | 16.3 | 8 | |
| 11.7 | 14 | 16.3 | 1 | CHANNEL |
| 5.8 | 7 | 8.2 | 2 | 2 3 |
| 2.9 | 3.5 | 4.1 | 3 | (5 mm Step Size) |
| 2.1 | 2.5 | 2.9 | 4 | Origin 0 mm |
| 2.1 | 2.5 | 2.9 | 5 | |
| 2.9 | 3.5 | 4.1 | 6 | |
| 5.8 | 7 | 8.2 | 7 | |
| 11.7 | 14 | 16.3 | 8 | |
| 11.7 | 14 | 16.3 | 1 | CHANNEL 4 |
| 6.7 | 8 | 9.3 | 2 | (5 mm Step Size) |
| 5.0 | 6 | 7 | 3 | Origin 1 mm |
| 6.7 | 8 | 9.3 | 4 | |
| 11.7 | 14 | 16.3 | 5 | |
| 173.6 | 208 | 242.4 | seconds | |

3.4

Ellipse Skin Applicator
80 IDL Rounded Aug. 25, 2010

| 5 Gy | 6 Gy | 7 Gy | Position | |
|---|---|---|---|---|
| 14.9 | 17.9 | 20.9 | 1 | CHANNEL 1 |
| 14.9 | 17.9 | 20.9 | 2 | (9 mm Step Size) |
| 12.5 | 15.0 | 17.5 | 1 | CHANNEL 2 |
| 0.0 | 0.0 | 0.0 | 2 | (8 mm Step Size) |
| 12.5 | 15.0 | 17.5 | 3 | |
| 14.9 | 17.9 | 20.9 | 1 | CHANNEL 3 |
| 14.9 | 17.9 | 20.9 | 2 | (9 mm Step Size) |
| 84.6 | 101.6 | 118.6 | seconds | |

Figure 7:
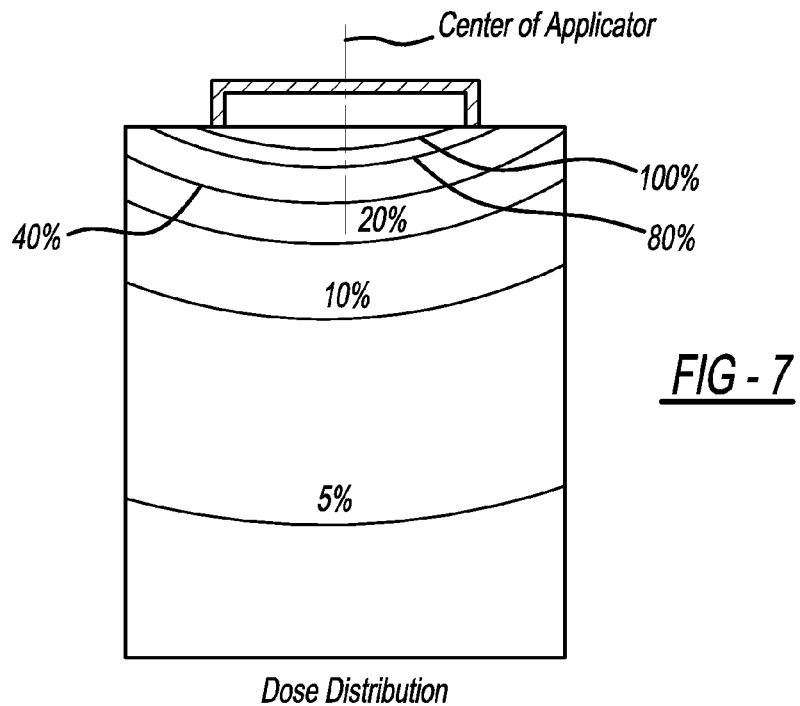
FIG. 7 is a percent dose distribution graph produced from using an embodiment of the present invention.

Now with reference to FIG. 7, an exemplary percent dose distribution (PDD) plot is shown which illustrates the integrated distribution of radiation across an applicator in accordance with this invention. The distribution integrates exposure of the radioisotope sources measured on the plane of patient treatment area 24 as they move along the guide paths in accordance with a schedule such as that described previously for 2 cm. applicator 36. The dose distribution plot shows a high degree of uniformity across the cross section of the patient treatment area 24. This is a primary feature of applicators in accordance with this invention as it is desirable to achieve a desired dose and apply the distribution uniformly across the patient treatment area 24.

Figure 8:
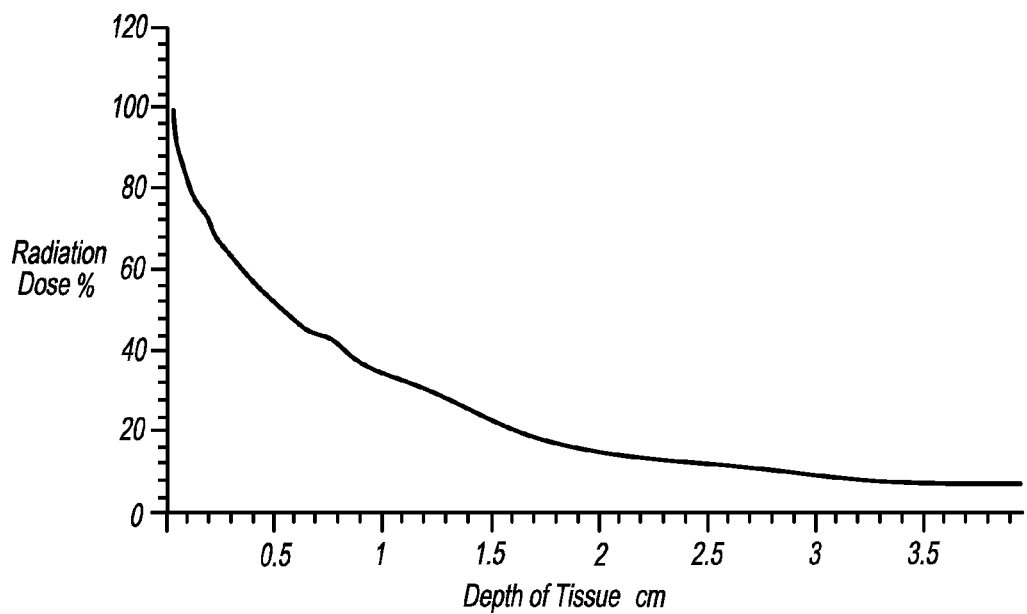
FIG. 8 is a vertical profile plot showing an integrated dose using an applicator in accordance with an embodiment of the present invention along the depth of penetration.

FIG. 8 shows an integrated dose distribution as a measured along the depth the present penetration, starting from the skin surface of patient treatment area 24 to deeper tissue. The curve shows a dramatic exposure drop off from the surface, which is a desirable attribute since the intent is to treat diseased tissue at the surface of the patient skin and it is not intended to penetrate deeper where underlying subcutaneous tissue can be damaged by undesired radiation exposure.

While the above description constitutes the preferred embodiment of the present invention, it will be appreciated that the invention is susceptible to modification, variation and change without departing from the proper scope and fair meaning of the accompanying claims.

The invention claimed is:
1. An applicator for use as part of a high dose rate brachytherapy system for use in topical irradiation of a skin surface area of a human patient, the system including a brachytherapy machine for positioning radioisotope sources at desired points along one or more source guides, the applicator comprising:

a cup shaped housing forming a bottom surface with a perimeter wall projecting from the bottom surface defining a concave cavity, the wall forming a perimeter generally planar face surface, the housing forming guide channel bores through the perimeter wall defining at least two HDR guide channels for receiving and mounting HDR guide tubes, the HDR guide channels oriented to cross the concave cavity and oriented parallel to the bottom surface and mutually parallel to one another, such that multiple source dwell positions are established at a single fixed distance from the bottom surface within the concave cavity that can be used to shape dose distribution patterns during the topical irradiation.

2. An applicator in accordance with claim 1 further comprising, the housing formed of tungsten.

3. An applicator in accordance with claim 1 further comprising, the guide channel bores forming a first open bores section and an aligned blind bore section.

4. An applicator in accordance with claim 1, wherein the housing further comprises a tubular source guide fixed in the guide channel bores.

5. An applicator in accordance with claim 4 further comprising a set screw positioned inside a fixing bore provided for and intersecting with each guide channel bore.

6. An applicator in accordance with claim 1 further comprising, the applicator forming two HDR guide channels.

7. An applicator in accordance with claim 1 further comprising, the applicator forming three HDR guide channels.

8. An applicator in accordance with claim 1 further comprising, the applicator forming four HDR guide channels.

9. An applicator in accordance with claim 1 further comprising, a filter affixed to the applicator and covering the concave cavity.

10. An applicator in accordance with claim 1 further comprising the applicator housing being generally circular in shape and having an outside diameter of about 2 cm and forming two of the guide channels.

11. An applicator in accordance with claim 1 further comprising the applicator housing being generally circular in shape and having an outside diameter of about 3 cm and forming three of the guide channels.

12. An applicator in accordance with claim 1 further comprising the applicator housing being generally circular in shape and having an outside diameter of about 4 cm and forming four of the guide channels.

13. An applicator in accordance with claim 1 further comprising the applicator housing having a generally elliptical shape and having an outside surface with major axes of about 2 cm and about 3 cm and forming three of the guide channels.

14. A brachytherapy system for use in topical irradiation of a skin surface area of a human patient, the system comprising:
a brachytherapy machine for positioning radioisotope sources at desired points on a pre-described time schedule along one or more source guides;
flexible transfer tubes coupled with the brachytherapy machine;
guide tubes coupled with the flexible transfer tubes;
an applicator in the form of a cup shaped housing forming a bottom surface with a perimeter wall projecting from the bottom surface defining a concave cavity, the wall forming a perimeter generally planar face surface, the housing forming guide channel bores through the perimeter wall defining at least two HDR guide channels for receiving and mounting HDR guide tubes, the HDR guide channels oriented to cross the concave cavity and oriented parallel to the bottom surface and mutually parallel to one another, such that multiple source dwell positions are established at a single fixed distance from the bottom surface within the concave cavity that can be used to shape dose distribution patterns during the topical irradiation; and
the guide tubes fixed within the applicator HDR guide channels, the guide tubes receiving a radioisotope radiation source positioned by the brachytherapy machine within the guide channels.

15. A brachytherapy system in accordance with claim 14 further comprising the brachytherapy machine moving the sources to a plurality of dwell positions along the guide tubes and within the applicator concave cavity for predetermined time periods.

16. A brachytherapy system in accordance with claim 14, wherein the housing further comprises a tubular source guide fixed in the guide channel bores.

17. A brachytherapy system in accordance with claim 14 further comprising the applicator forming two guide channels.

18. A brachytherapy system in accordance with claim 14 further comprising the applicator forming three guide channels.

19. A brachytherapy system in accordance with claim 14 further comprising the applicator forming four guide channels.

20. A brachytherapy method for topical irradiation of a skin surface area of a human patient, the method comprising:
providing a brachytherapy machine for positioning radioisotope sources at desired points along two or more source guides;
providing two or more flexible transfer tubes coupled with the brachytherapy machine;
providing an applicator in the form of a cup shaped housing forming a bottom surface with a perimeter wall projecting from the bottom surface defining a concave cavity, the wall forming a perimeter generally planar face surface, the housing forming guide channel bores through the perimeter wall defining at least two HDR guide channels for receiving and mounting HDR guide tubes, the HDR guide channels oriented to cross the concave cavity and oriented parallel to the bottom surface and mutually parallel to one another, such that multiple source dwell positions are established at a single fixed distance from the bottom surface within the concave cavity that can be used to shape dose distribution patterns during the topical irradiation;
providing guide tubes;
coupling the guide tubes to the flexible transfer tubes;
fixing the guide tubes within the applicator guide channels;
positioning the applicator at a position relative to a patient treatment area; and
guiding a radioisotope radiation source positioned by the brachytherapy machine within each of the guide channels to irradiate the patient treatment area.

21. A brachytherapy method in accordance with claim 20 further comprising the steps of; providing the applicator having two of the guide channels.

22. A brachytherapy method in accordance with claim 20 further comprising the steps of providing the applicator having three of the guide channels.

23. A brachytherapy method in accordance with claim 20 further comprising the steps of providing the applicator having four of the guide channels.

24. A brachytherapy method in accordance with claim 20 wherein the step of guiding further comprises positioning the radioisotope radiation source at a plurality of positions within each of the guide channels.

25. A brachytherapy method in accordance with claim 20 further comprising the steps of using the brachytherapy method for the treatment of squamous cell skin cancers.

26. A brachytherapy method in accordance with claim 20 further comprising the steps of using the brachytherapy method for the treatment of basal cell skin cancers.

* * * * *